US00PP23697P2

(12) United States Plant Patent
Donahue

(10) Patent No.: US PP23,697 P2
(45) Date of Patent: Jul. 2, 2013

(54) ***LANTANA* PLANT NAMED 'ELESHINE'**

(50) Latin Name: *Lantana camara*
Varietal Denomination: ELESHINE

(76) Inventor: Mitchell Donahue, Indian Trail, NC (US)

( * ) Notice: Subject to any disclaimer, the term of this patent is extended or adjusted under 35 U.S.C. 154(b) by 0 days.

(21) Appl. No.: 13/200,511

(22) Filed: Sep. 23, 2011

(51) Int. Cl.
*A01H 5/00* (2006.01)

(52) U.S. Cl.
USPC ..... Plt./227

(58) Field of Classification Search
USPC ..... Plt./227
See application file for complete search history.

*Primary Examiner* — Kent L Bell
(74) *Attorney, Agent, or Firm* — Cassandra Bright

(57) ABSTRACT

A new and distinct *Lantana* cultivar named 'ELESHINE' is disclosed, characterized by a short, outwardly spreading habit. The new variety produces bright yellow flowers changing to white with age. Plants are highly floriferous. The new variety is a *Lantana*, normally produced as an outdoor garden or container plant.

3 Drawing Sheets

Figure 1:
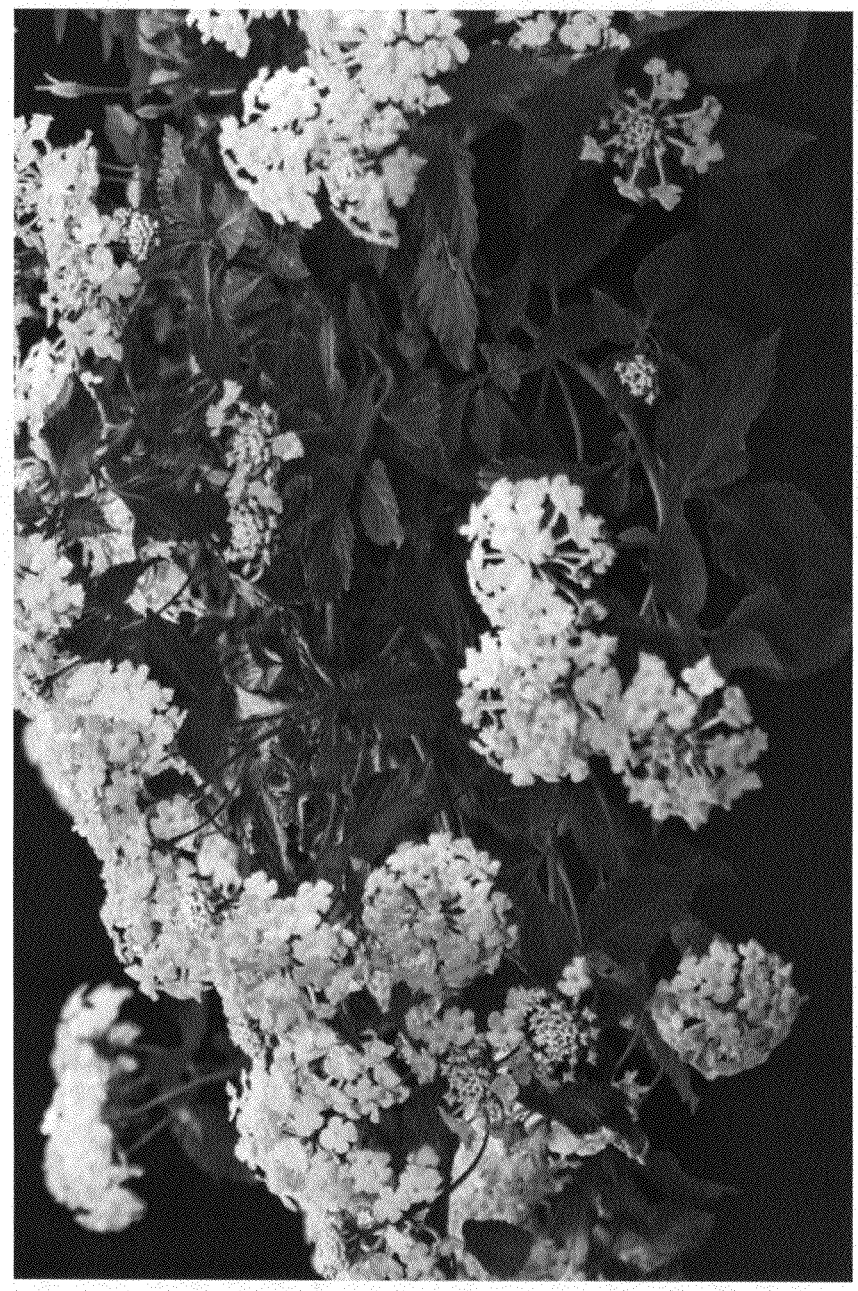

Latin name of the genus and species: *Lantana camara.*
Variety denomination: 'ELESHINE'.

BACKGROUND OF THE INVENTION

The new *Lantana* cultivar is a product of a planned breeding program conducted by the inventor, Mitch Donahue, a citizen of the United States. The objective of the breeding program was to produce new *Lantana* varieties for ornamental commercial applications. The cross resulting in this new variety was made during August 2010 at a commercial nursery in Indian Trail, N.C.

The new variety is the result of an open pollination, the seed parent is the unpatented variety *Lantana camara* 'Megan's Gold', and the pollen parent is unknown. The new variety was discovered in May 2011 by the inventor in a trial field of seedlings resulting from the 2010 crossing, at the commercial nursery in Indian Trail, N.C.

Asexual reproduction of the new cultivar 'ELESHINE' by vegetative cuttings was first performed at a commercial greenhouse in Indian Trail, N.C. in May 2011. Subsequently, at least two generations have been produced, and have shown that the unique features of this cultivar are stable and reproduced true to type in successive generations.

SUMMARY OF THE INVENTION

The cultivar 'ELESHINE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ELESHINE'. These characteristics in combination distinguish 'ELESHINE' as a new and distinct *Lantana* cultivar:

1. Bright yellow flower color
2. Low growing, outwardly spreading plant habit

3. Highly floriferous
4. Flowers change from yellow to white with age.

PARENT COMPARISON

Plants of the new cultivar 'ELESHINE' are comparable to the seed parent *Lantana camara* 'Megan's Gold', unpatented. The two *Lantana* varieties are similar in most horticultural characteristics however, the new variety 'ELESHINE' differs in having brighter yellow flowers, than the seed parent variety. Flower color of the new variety changes with age, whereas the seed parent does not exhibit flower color change with age. Additionally plants of 'ELESHINE' are shorter, more outwardly spreading and more floriferous than plants of 'Megan's Gold'.

COMMERCIAL COMPARISON

Plants of the new cultivar 'ELESHINE' are comparable to the variety *Lantana camara* 'Sunny Side Up', patent status unknown, after reasonable search by the applicant. The two *Lantana* varieties are similar in most horticultural characteristics however, the new variety 'ELESHINE' differs in having brighter yellow flowers. Additionally plants of 'ELESHINE' are much shorter and more floriferous than plants of 'Sunny Side Up'. Plants of 'ELESHINE' also spread laterally much more than 'Sunny Side Up'.

Plants of the new cultivar 'ELESHINE' are comparable to the commercial variety *Lantana* 'Golden Zinger' unpatented. The two *Lantana* varieties are similar in most horticultural characteristics however, plants of the new variety 'ELESHINE' differ in having flowers that are more yellow. Additionally plants of 'ELESHINE' are much shorter and more floriferous than plants of 'Golden Zinger'. Plants of 'ELESHINE' also spread laterally much more than 'Sunny Side Up'.

BRIEF DESCRIPTION OF THE PHOTOGRAPHS

FIG. 1: Illustrates in full color a closeup view of blooms and buds.

Figure 2:
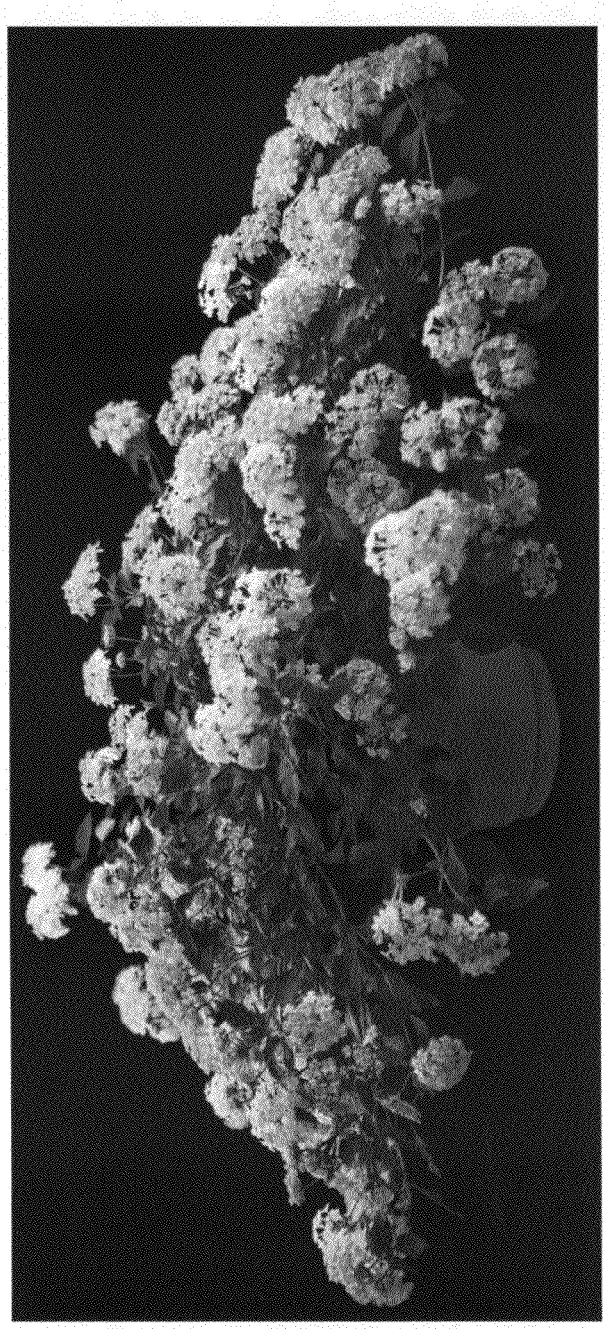

FIG. 2: Illustrates in full color 'ELESHINE' in a 1 gallon pot at approximately 8 weeks old from a rooted cutting.

Figure 3:
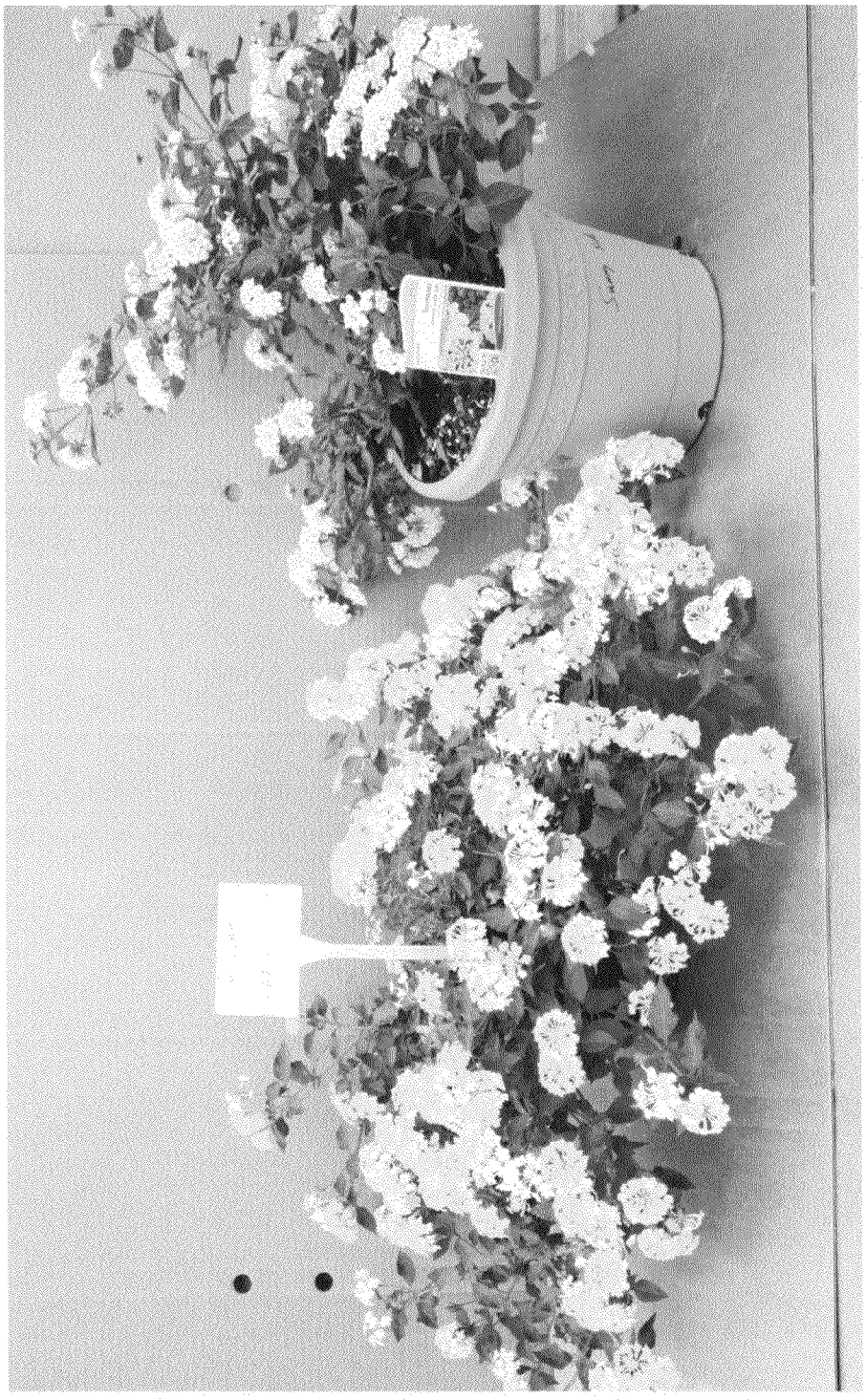

FIG. 3: Shows a comparison of plants of 'ELESHINE' with 'Sunny Side Up' Plants are the same age. Plants of 'ELESHINE' are on the left hand side of the photo, 'Sunny Side Up' plants are on the right.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'ELESHINE' plants grown 8 weeks outdoors during Spring in Indian Trail, N.C. The growing temperature ranged from 14° C. to 20° C. during the night and from 22° C. to 35° C. during the day. General light conditions are bright, normal sunlight. Measurements and numerical values represent averages of typical plant types.

Botanical classification: *Lantana camara* 'ELESHINE'.

PROPAGATION

Time to initiate roots: 6 to 8 days at approximately 15° C.

Root description: Fibrous.

PLANT

Growth habit: Spreading.

Pot size of plant described: 16 cm.

Height: 16 cm.

Plant spread: 79 cm.

Growth rate: Faster Than Typical For Most *Lantana*.

Branching characteristics: Freely Branches at each internode with two lateral branches.

Length of primary lateral branches: 39 cm.

Diameter of lateral branches: 0.3 cm.

Quantity of primary lateral branches: 4.

Characteristics of primary lateral branches:

*Form*.—Squared.

*Diameter*.—0.3 cm.

*Color*.—Near Green 143B at tip changing to Greyed-Green 195A.

*Texture*.—Pubescent.

*Strength*.—Soft/Very Flexible.

Internode length: 3-4 cm.

FOLIAGE

Leaf:

*Arrangement*.—Opposite.

*Quantity*.—Approximately 16-18 per branch.

*Average length*.—4.5 cm.

*Average width*.—2.2 cm.

*Shape of blade*.—Ovate.

*Apex*.—Pointed.

*Base*.—Attenuate.

*Margin*.—Serrated.

*Texture of top surface*.—Rough/Pubescent.

*Texture of lower surface*.—Rough/Pubescent.

*Aspect*.—Flat.

*Color*.—Young foliage upper side: Closest to Green 139A. Young foliage under side: Green 138B. Mature foliage upper side: Closest to Green 139A. Mature foliage under side: Green 137C.

*Venation*.—Type: Pinnate. Venation color upper side: Yellow-Green 144B. Venation color under side: Green 138B.

*Petiole*.—Length: 0.7 cm. Diameter: 0.2 cm. Color: Green 138A. Texture: Smooth/Slightly Pubescent.

FLOWER

Natural flowering season: Continuous Flowers In Warm Climate.

Days to flowering from rooted cutting: 28.

Inflorescence and flower type and habit: Corymb.

Average flowers per inflorescence: Approximately 25 to 35 flowers and buds.

Rate of flower opening: 4 to 5 days from bud to fully opened flower.

Flower longevity on plant: 8-10 days.

Persistent or self-cleaning: Self Cleaning.

Overall inflorescence size:

*Height*.—Approximately 1.0 cm.

*Diameter*.—Approximately 3.1 cm.

Individual flower size:

*Height*.—Approximately 1.1 cm including corolla tube.

*Diameter*.—Approximately 0.9 cm.

Bud:

*Shape*.—Square/Pillow Shaped.

*Length*.—1.2 cm Including Corolla Tube.

*Diameter*.—0.3 cm.

*Color*.—Yellow 13A — Young Bud 1D.

Corolla:

*Petals/lobes*.—Number: 4. Length: 0.5 cm upper — 0.6 cm lower — 0.5 cm lateral petals. Width: 0.5 cm upper — 0.7 cm lower — 0.4 cm lateral petals. Shape: Broad deltate. Aspect: Slightly cupped with a long slender tube. Apex: Obtuse. Margin: Entire. Texture: Soft. Color: When opening: Upper surface: Yellow 9A. Lower surface: Yellow 7A. Fully opened:

*Upper surface*.—Closest to Yellow 12A but Shinier. Changes to White 155D on Oldest Blooms — Two Days before Blooms Drop.

*Lower surface*.—Yellow 3A Changes to White 155A on Oldest Blooms — Two Days before Bloom Drop. Throat/tube: Color: Yellow 5B changes to White 155C on older blooms. Texture: Smooth. Tube color: Yellow 12B (Bud) to Yellow 13B (Fully Open).

*Calyx/sepals*.—Form: 5 Sepals fused into a single tube. Calyx Length: 0.3 cm. Calyx Diameter: 0.1 cm. Sepal base: Fused. Sepal apex: Acute. Sepal texture: Smooth. Sepal color: Upper surface: Green 138D. Lower surface: Green 138D.

Flower bracts/inflorescence bracts:

*Appearance*.—Matte.

*Length*.—Approximately 0.7 cm

*Width*.—Approximately 0.1 cm.

*Shape*.—Narrow deltoid.

*Aspect*.—Cupped.

*Apex*.—Pointed.

*Margin*.—Entire.

*Texture*.—Upper (inner) and lower (outer) surfaces: Smooth.

*Color*.—Upper (inner) and lower (outer) surfaces: Upper — Green 137B-Lower — Green 138C.

Peduncles:
*Length*.—Approximately 3.6-5.0 cm.
*Diameter*.—Approximately 0.1 cm.
*Angle*.—About 45 degrees.
*Strength*.—Strong.
*Texture*.—Pubescent.
*Color*.—Yellow-Green 144A.

Pedicels:
*Length*.—Approximately 0.2 cm.
*Diameter*.—Approximately 0.1 cm.
*Angle*.—Range from 15 to 75 degrees.
*Strength*.—Moderately strong, very flexible.
*Texture*.—Lightly pubescent.
*Color*.—Yellow-Green 144C.
*Flower fragrance*.—Mild.

REPRODUCTIVE ORGANS

Stamens:
*Number* (*per flower*).—4.
*Filament length*.—0.1 cm.
*Anthers*.—Shape: Ovate. Length: 0.1 cm. Color: Brown 200B.

Pollen:
*Color*.—Near RHS Greyed-Yellow 161C.
*Amount*.—Sparse To None.

Pistils:
*Quantity per flower*.—1.
*Length*.—0.4 cm.
*Styles*.—Length: 0.3 cm. Color: Yellow-Green 144B.
*Ovary color*.—Green 138A.
*Stigma*.—Shape: Oval. Color: Yellow-Green 144A.

OTHER CHARACTERISTICS

Seed: Very little seed produced.
*Seed diameter*.—0.1 cm. Seed Color: Black 202A.

Fruit: Drupe.
*Young fruit*.—Drupe; Diameter: 0.3 cm. Color: Yellow-Green 146A.
*Older fruit*.—Diameter: 0.2 cm. Color: Black 202A.

Disease/pest resistance: Neither resistance nor susceptibility to pathogens and pests common to *Lantana* have been observed.

Temperature tolerance: The new variety tolerates temperatures between 0 to 40° C.

What is claimed is:

1. A new and distinct cultivar of *Lantana* plant named 'ELESHINE' as herein illustrated and described.

* * * * *